US011506665B2

(12) United States Patent
Müller et al.

(10) Patent No.: US 11,506,665 B2
(45) Date of Patent: Nov. 22, 2022

(54) METABOLIC BIOMARKER SET FOR ASSESSING OVARIAN CANCER

(71) Applicant: Biocrates Life Sciences AG, Innsbruck (AT)

(72) Inventors: Udo Müller, Innsbruck (AT); Simon Schafferer, Zirl (AT); Barbara Burwinkel, Heidelberg (DE)

(73) Assignee: BIOCRATES LIFE SCIENCES AG, Innsbruck (AT)

( * ) Notice: Subject to any disclaimer, the term of this patent is extended or adjusted under 35 U.S.C. 154(b) by 344 days.

(21) Appl. No.: 16/478,819

(22) PCT Filed: Jan. 18, 2018

(86) PCT No.: PCT/EP2018/051254
§ 371 (c)(1),
(2) Date: Jul. 17, 2019

(87) PCT Pub. No.: WO2018/134329
PCT Pub. Date: Jul. 26, 2018

(65) Prior Publication Data
US 2020/0386762 A1   Dec. 10, 2020

(30) Foreign Application Priority Data

Jan. 18, 2017  (EP) .................................... 17152072

(51) Int. Cl.
*G01N 33/574* (2006.01)
*G01N 33/68* (2006.01)
*G01N 33/92* (2006.01)
*G01N 33/48* (2006.01)

(52) U.S. Cl.
CPC ....... *G01N 33/57449* (2013.01); *G01N 33/68* (2013.01); *G01N 33/92* (2013.01); *G01N 33/48* (2013.01); *G01N 33/6848* (2013.01); *G01N 2405/04* (2013.01); *G01N 2405/08* (2013.01)

(58) Field of Classification Search
CPC .......... G01N 2405/04; G01N 2405/08; G01N 33/48; G01N 33/57449; G01N 33/68; G01N 33/6848; G01N 33/92; G01N 2800/36; G01N 2800/50; G01N 2800/52; G01N 2800/56; G01N 2800/7028; Y10T 436/173845; Y10T 436/24
USPC .......... 436/63, 64, 161, 173, 86, 89, 71, 111
See application file for complete search history.

(56) References Cited

U.S. PATENT DOCUMENTS

2011/0143444 A1* 6/2011 Muramatsu ............ G16B 40/20
                                                          436/90
2012/0004854 A1  1/2012 Fernandez et al.
2012/0129265 A1  5/2012 Lundin et al.
2017/0097355 A1* 4/2017 Raftery ............ G01N 33/57449
2017/0285036 A1* 10/2017 Hilvo ...................... G01N 33/64
2019/0383819 A1* 12/2019 Nagourney .......... G01N 33/574

FOREIGN PATENT DOCUMENTS

| CN | 101832977 A | 9/2010 |
|---|---|---|
| JP | 2005-509870 A | 4/2005 |
| JP | 2008-547031 A | 12/2008 |
| WO | 03/44213 A2 | 5/2003 |
| WO | WO-2007003343 A1 | 1/2007 |
| WO | WO-2007003344 A2 | 1/2007 |
| WO | 2009/154296 A1 | 12/2009 |
| WO | WO-2009151967 A1 | 12/2009 |
| WO | WO-2010/139341 A1 | 12/2010 |
| WO | 2012/164525 A2 | 12/2012 |
| WO | WO-2016038157 A1 | 3/2016 |
| WO | 2016/051020 A1 | 4/2016 |
| WO | 2018/136085 * | 7/2018 |

OTHER PUBLICATIONS

Plewa et al. Life Sciences, vol. 222, Mar. 7, 2019, pp. 235-244.*
Bachmayr-Heyda et al., "Integrative Systemic and Local Metabolomics with Impact on Survival in High-Grade Serous Ovarian Cancer," *Clinical Cancer Research*, vol. 23, No. 8, pp. 2081-2092, 2017.
Ke et al., "Large-scale profiling of metabolic dysregulation in ovarian cancer," *International Journal of Cancer*, vol. 136, pp. 516-526, 2015.
Ke et al., "Metabolic phenotyping for monitoring ovarian cancer patients," *Scientific Reports*, 6:23334, 2016.
Alonezi et al., "Metabolomic Profiling of the Effects of Melittin on Cisplatin Resistant and Cisplatin Sensitive Ovarian Cancer Cells Using Mass Spectrometry and Biolog Microarray Technology," *Metabolites*, 6(4): 35, 2016.
Zhang et al., "High resolution mass spectrometry coupled with mutlivariate data analysis revealing plasma lipidomic alteration in ovarian cancer in Asian women," *Talanta*, vol. 150, pp. 88-90, 2016.
Guan et al., "Ovarian cancer detection from metabolomic liquid chromatography/mass spectrometry data by support vector machines," *BMC Bioinformatics*, 10:259, 2009.
Turkoglu et al., "Metabolomics of biomarkers discovery in ovarian cancer: a systematic review of the current literature," *Metabolomics*, 12:60, 2016.
International Search Report for PCT/EP2018/051254 dated Mar. 19, 2018.
Written Opinion of the International Searching Authority for PCT/EP2018/051254 dated Mar. 19, 2018.
"Absolute IDQR p400HR kit," retrieved from http://www.biocrates.com/products/research-products/absoluteidq-p400-hr-kit, retrieved on Mar. 6, 2018, pp. 5.

(Continued)

*Primary Examiner* — Maureen Wallenhorst
(74) *Attorney, Agent, or Firm* — Faegre Drinker Biddle & Reath LLP

(57) ABSTRACT

The present invention relates to new biomarkers for assessing ovarian cancer being more sensitive, particularly at early stage of disease. Moreover, the present invention relates to a method for assessing ovarian cancer from a patient to be examined, and to a kit for carrying out the method.

9 Claims, 9 Drawing Sheets

(56) References Cited

OTHER PUBLICATIONS

International Preliminary Report on Patentability received for PCT Patent Application No. PCT/EP2018/051254, dated Apr. 1, 2019, 6 pages.
Zhang et al., "Prediction of advanced ovarian cancer recurrence by plasma metabolic profiling", Molecular Biosystems, vol. 11, No. 2, Jan. 1, 2015, pp. 516-521.

* cited by examiner

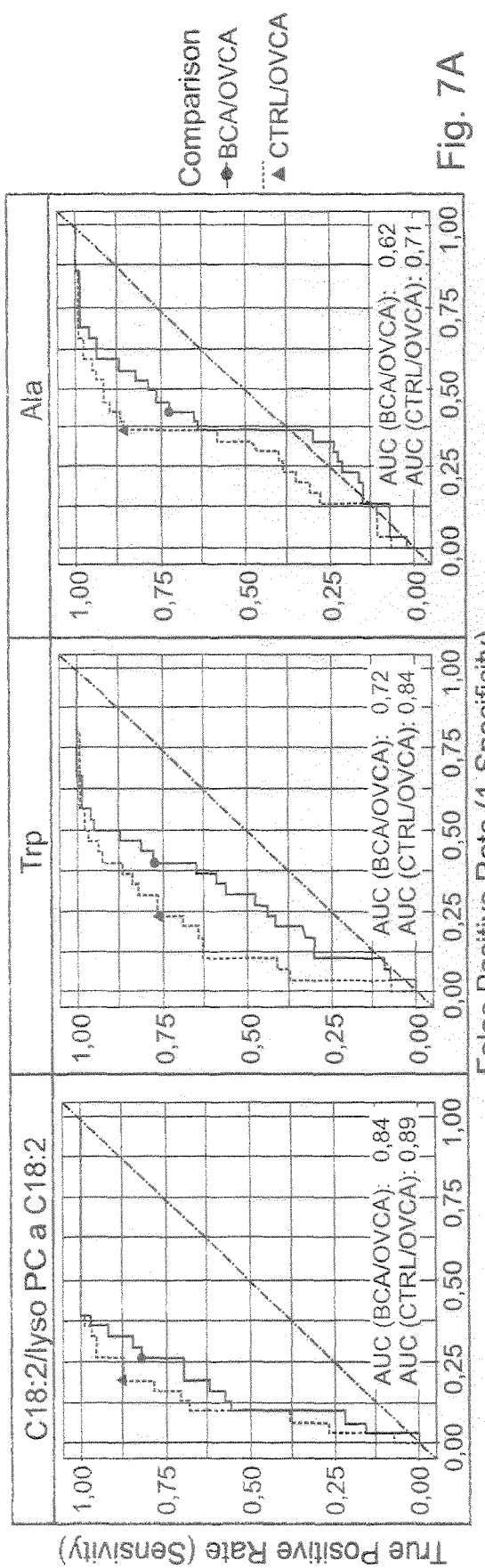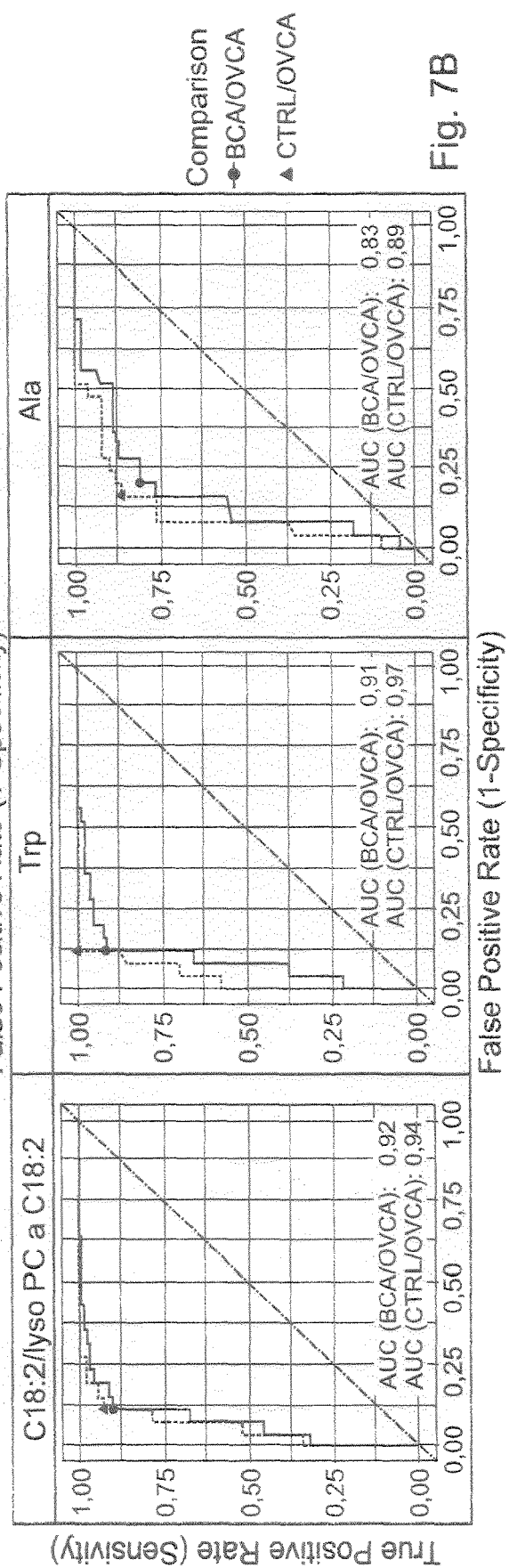
Fig. 7A
Fig. 7B

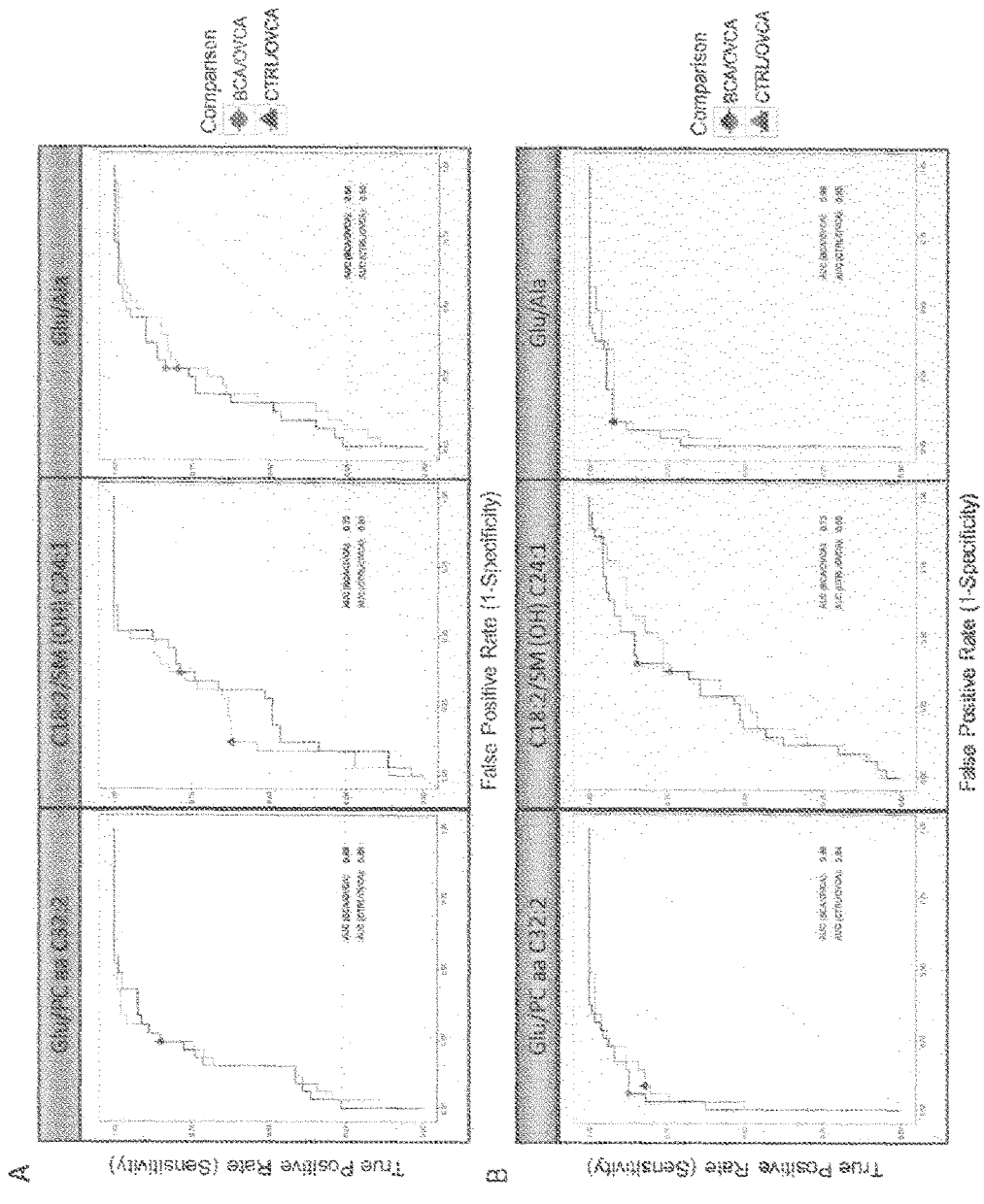

METABOLIC BIOMARKER SET FOR ASSESSING OVARIAN CANCER

CROSS-REFERENCE TO RELATED APPLICATIONS

This application is a national stage application (under 35 U.S.C. § 371) of PCT/EP2018/051254, filed Jan. 18, 2018, which claims benefit of European Application No. 17152072.9, filed Jan. 18, 2017, both of which are incorporated herein by reference in their entirety.

The present invention relates to new biomarkers for assessing ovarian cancer being more sensitive, particularly at early stage of disease. Moreover, the present invention relates to a method for assessing ovarian cancer from a patient to be examined, and to a kit for carrying out the method.

Metabolomics is a comprehensive quantitative measurement of low molecular weight compounds covering systematically the key metabolites, which represent the whole range of pathways of intermediary metabolism. In a systems biology approach, it provides a functional readout of changes determined by genetic blueprint, regulation, protein abundance and modification, and environmental influence. The capability to analyse large arrays of metabolites extracts biochemical information reflecting true functional endpoints of overt biological events while other functional genomics technologies such as transcriptomics and proteomics, though highly valuable, merely indicate the potential cause for phenotypic response. Therefore, they cannot necessarily predict drug effects, toxicological response or disease states at the phenotype level unless functional validation is added.

Metabolomics bridges this information gap by depicting in particular such functional information since metabolite differences in biological fluids and tissues provide the closest link to the various phenotypic responses. Needless to say, such changes in the biochemical phenotype are of direct interest to pharmaceutical, biotech and health industries once appropriate technology allows the cost-efficient mining and integration of this information.

In general, phenotype is not necessarily predicted by genotype. The gap between genotype and phenotype is spanned by many biochemical reactions, each with individual dependencies to various influences, including drugs, nutrition and environmental factors. In this chain of biomolecules from the genes to phenotype, metabolites are the quantifiable molecules with the closest link to phenotype. Many phenotypic and genotypic states, such as a toxic response to a drug or disease prevalence are predicted by differences in the concentrations of functionally relevant metabolites within biological fluids and tissue.

Ovarian cancer (OC) is the second most common and most lethal of all gynaecologic diseases, displaying a worldwide increase of incidence and prevalence over the past decade. In Europe, women diagnosed between the years 2000 and 2007 showed a mean five-year survival of only around 35%. In the United States more than 20,000 new ovarian cancer cases are expected each year leading to over 14,000 deaths (Siegel et al. 2015). Despite receiving aggressive combined treatment strategies including adjuvant chemotherapy and debulking surgery, the five year survival rate is even less than 25% for women diagnosed with advanced ovarian cancer stages III or IV (Shapira et al. 2014; Berkenblit and Cannistra 2005; Vaughan et al. 2011). Therefore, a reliable diagnosis with validated methods that could detect ovarian cancer with a high sensitivity in order to correctly assign women with the disease and specificity to avoid false-positive results would be essential.

The currently applied screening tools for ovarian cancer are mainly based on imaging methods such as transvaginal sonography, pelvic examination or protein biomarkers. CA-125 (Cancer Antigen 125) and HE4 (Human Epididymis Secretory Protein 4) are the only two protein-markers for ovarian cancer monitoring, which have been approved by the U.S. Food and Drug Administration (FDA). An increase in blood concentrations of CA-125 can be used as an indicator of disease recurrence (Suh et al. 2010). However, elevated levels of soluble CA-125 has also been found in a variety of other malignancies such as breast cancer, lymphomas, endometriosis or gastric cancer (Norum et al. 2001; Yamamoto et al. 2007; Bairey et al. 2003; Kitawaki et al. 2005). Therefore, due to its limited specificity and sensitivity, CA-125 alone cannot serve as an ideal biomarker for ovarian cancer. Notably, CA-125 together with transvaginal sonography is only able to detect around 30% of women with early-stage ovarian cancer (Roupa et al. 2004). Previous studies indicated that the combination of CA-125 and HE4 levels in serum samples might produce a method with increased sensitivity and specificity in identifying ovarian cancer. In addition, a recently developed Risk of Malignancy Algorithm (ROMA) that integrates both CA-125 and HE4 with the menopausal status of women has been approved by the FDA for distinguishing malignant from benign pelvic masses, showing an overall better performance in the pre-menopausal women than postmenopausal (Moore et al. 2011; Wei et al. 2016).

However, the accuracy for the most commonly used single serum markers CA-125 and HE4 are controversial or insufficient and there is a future need for non-protein based biomarkers such as metabolites for the solid diagnosis and screening for ovarian cancer.

Since Ovarian Cancer is thought to be treatable and preventable at earlier stages an earlier detection would ease patients from complications or suffering and reduce health care costs for both public health systems and the patients themselves.

In view of the above-mentioned problems existing in the prior art, the object underlying the present invention is the provision of new biomarkers for assessing ovarian cancer which markers are more sensitive, particularly at early stage of disease. Optimally, the marker should be easily detectable in a biological sample such as in blood and/or plasma, its level should be consistently related to the degree of ovary injury and its level should change. Moreover, it is an object of the present invention to provide for a method for assessing ovarian cancer in a biological sample.

In order to solve the objects underlying the present invention the inventors based their investigations on metabolomics as it could give insight in the biochemical changes occurring in the ovary during the course of disease and offer several novel and potentially improved biomarkers. Hence, it would be a significant improvement to have metabolic biomarkers for ovarian cancer, which would also give more information about the function of the ovary and the biochemical reactions therein. The inventors found that a more comprehensive picture of all involved pathways and mechanisms is realised when using a panel of metabolites that are altered with progressing ovarian cancer rather than employing only single-markers as provided in the prior art.

SUMMARY OF THE INVENTION

Therefore, the present invention, as presented in the claims, provides for new biomarkers (i.e. a new biomarker set) suitable for assessing ovarian cancer which are more sensitive for pathological changes in the ovary, particularly at early stage of disease. Moreover, the present invention also provides for a method for assessing ovarian cancer in a patient, as well as a kit adapted to carry out the method.

DESCRIPTION OF THE PREFERRED EMBODIMENTS

By employing the specific (set of) biomarkers and the method according to the present invention it has become possible to more properly and reliably assess ovarian cancer.

"Assessment" or "Assessing" in the sense of the present invention means the diagnosis or prediction of the onset and monitoring of the progression of the disease, in particular the detection and marking of the disease at the different stages.

The present invention allows to predict and diagnose ovarian cancer in an improved manner and at an early stage of the disease and provides a more sensitive detection for pathological changes in the ovary. In fact, the biomarkers according to the invention are easily detectable in samples, in particular in blood and/or in plasma, their level is consistently related to the degree of ovary disease/injury and their level changes.

In general, a biomarker is a valuable tool due to the possibility to distinguish two or more biological states from one another, working as an indicator of a normal biological process, a pathogenic process or as a reaction to a pharmaceutical intervention. A metabolite is a low molecular compound (<1 kDa), smaller than most proteins, DNA and other macromolecules. Small changes in activity of proteins result in huge changes in the biochemical reactions and their metabolites (=metabolic biomarker, looking at the body's metabolism), whose concentrations, fluxes and transport mechanisms are sensitive to diseases and drug intervention. This enables getting an individual profile of physiological and pathophysiological substances, reflecting both genetics and environmental factors like nutrition, physical activity, gut microbial and medication. Thus, a metabolic biomarker provides more comprehensive information than for example a protein or hormone which are biomarkers, but even not metabolic biomarkers.

In view, thereof, the term metabolic biomarker as used herein is defined to be a compound suitable as an indicator of the state of ovarian cancer, being a metabolite or metabolic compound occurring during metabolic processes in the mammalian body.

The metabolic biomarker (set) measured according to the present invention comprises the following species of metabolites (i.e. analytes) at least i.) one amino acid selected from the group of alanine, arginine, histidine, tryptophan, glutamate, and
ii.) one phospholipid selected from the group of lyso PC a C18:1, lyso PC a C18:2, and PC aa C32:2, and
iii.) one acylcarnitine selected from the group of acylcarnitine C18:1, acylcarnitine C18:2, and optional
iv.) one sphingolipid SM(OH)C24:1,
and wherein at least one ratio of at least two biomarkers of i.) to iv.) is determined
at the same time allowing a more reliable diagnosis of ovarian cancer, in particular related to FIGO stages I and II, see below. Such a fact has neither been described in nor made obvious from the prior art.

Hence, the present invention refers to a metabolic biomarker set comprising or consisting of the following species of metabolites i.) one amino acid selected from the group of alanine, arginine, histidine, tryptophan, glutamate, and
ii.) one phospholipid selected from the group of lyso PC a C18:1, lyso PC a C18:2, and PC aa C32:2, and
iii.) one acylcarnitine selected from the group of acylcarnitine C18:1, preferably acylcarnitine C18:2, and optional
iv.) one sphingolipid SM(OH)C24:1.

Moreover, the present invention relates to a method for assessing, in particular diagnosing ovarian cancer, obtaining a sample, preferably blood and/or plasma, from a patient to be examined and determining in the sample the amount of at least i.) one amino acid selected from the group of alanine, arginine, histidine, tryptophan, glutamate, and
ii.) one phospholipid selected from the group of lyso PC a C18:1, lyso PC a C18:2, and PC aa C32:2, and
iii.) one acylcarnitine selected from the group of acylcarnitine C18:1, preferably acylcarnitine C18:2, and optional
iv.) one sphingolipid SM(OH)C24:1 are determined,
and wherein at least one ratio of at least two biomarkers of i.) to iv.) is determined.

The definitions of the related classes and species are known to the skilled person in the art, however, preferred members of these classes are summarized in Table 1 below directed to amino acids, biogenic amines, acylcarnitines, hexoses, sphingolipids and glycerophospholipids.

The metabolic biomarker set and related method may be extended with at least one metabolite according to Table 1 presenting species of the above-mentioned classes.

It has surprisingly been found that measuring a set of biomarkers comprising these classes and species of metabolites allows to predict and diagnose ovarian cancer in an improved manner and at an early stage of the disease. In particular, it allows a more sensitive detection for pathological changes in the ovary. If one class or specie of metabolites of this group is omitted or if the number thereof is decreased the assessment of ovarian cancer becomes less sensitive and less reliable. This particularly applies for the early stages of the disease being not reliably-detectable according to known methods using known biomarkers at all. In fact, at least i.) one amino acid selected from the group of alanine, arginine, histidine, tryptophan, glutamate, and
ii.) one phospholipid selected from the group of lyso PC a C18:1, lyso PC a C18:2, and PC aa C32:2, and
iii.) one acylcarnitine selected from the group of acylcarnitine C18:1, preferably acylcarnitine C18:2, and optional
iv.) one sphingolipid SM(OH)C24:1 are determined,
and wherein at least one ratio of at least two biomarkers of i.) to iv.) is determined.

In a preferred embodiment of the invention the biomarker set or related method further comprises the measurement of a ratio of selected biomarkers, in particular at least one ratio of at least two biomarkers of i.) to iv.) is determined. By measuring these ratio(s) the diagnostic performance of the biomarker set and the method according to the invention can be further improved.

The metabolomic set of biomarker are measured and the amount is preferably assessed by electrospray ionization tandem mass spectrometry in MRM mode using internal standard calibration, the said ratio can be determined by quantification of the single metabolites and calculating the ratios (e.g. C18:2/lyso PC a C18:2=0.00167 with c(C18:2)=37.074 μM and c(lyso PC a C18:2)=0.062 μM) and accordingly measuring the concentrations of the target analytes and calculating the ratios. However, the said ratio has a value of greater than zero.

More preferably, the biomarker set or related method according to the invention further comprises one or more metabolites selected from the group of amino acids, biogenic amines, acylcarnitines, hexoses, sphingolipids and glycerophospholipids. Preferred examples of these classes are presented in Table 1 below. Again, by measuring in addition metabolites of these classes the diagnostic performance of the biomarker set and the method according to the invention can be further improved.

A particularly preferred biomarker set or related method is the one wherein the amino acids are selected from arginine, tryptophan, and/or the ratios are selected from C18:2/lysoPC a C18:2, C18:2/SM (OH) C24:1, Glu/Ala, Glu/PC aa C32:2.

In one embodiment of the method according to the invention body fluid, preferably blood, is drawn from the patient to be examined, optionally full blood or serum, or available plasma, and the diagnosis is carried out in vitro/ex vivo, e.g. outside of the human or animal body.

The invention therefore also relates to identifying patients having an increased risk and/or an unfavourable prognosis of ovarian cancer, especially in symptomatic and/or asymptomatic patients.

Therefore, the invention also relates to a method for the diagnosis and/or risk classification of patients having ovarian cancer for carrying out clinical decisions, such as the continuative treatment and therapy by means of pharmaceuticals, including the decision of hospitalization of the patient.

In a further preferred embodiment of the method according to the invention the assessment is for the diagnosis and/or risk classification, for the prognosis, for differential diagnostic, for early stage detection and recognition.

The term "ovarian cancer" refers to a type of gynecologic tumors having no or few symptoms in the early stage of a patient or female patient. Ovarian cancer is a malignant disease of the ovary in the genital tract in women, (cf. Pschyrembel, de Gruyter, 263rd edition (2012), Berlin).

Within the scope of this invention, the term "patient, in particular female patient" is understood to mean any test subject (human or mammal), with the provision that the test subject is tested for ovarian cancer. The term "female patient" is understood to mean any female test subject.

Moreover, the invention relates to a kit adapted for carrying out the method, wherein the kit comprises a device which contains one or more wells and one or more inserts impregnated with at least one internal standard. Such a device is in detail described in WO 2007/003344 and WO 2007/003343.

For the measurement or determination of the metabolite concentrations/amounts including ratios in the sample a quantitative analytical method such as chromatography, spectroscopy, and mass spectrometry is to be employed, while mass spectrometry is particularly preferred. The chromatography may comprise GC, LC, HPLC, and UPLC; spectroscopy may comprise UV/Vis, IR, and NMR; and mass spectrometry may comprise ESI-QqQ, ESI-QqTOF, MALDI-QqQ, MALDI-QqTOF, and MALDI-TOF-TOF. Preferred is the use of FIA- and HPLC-tandem mass spectrometry. These analytical methods are generally known to the skilled person.

For measuring or determining the metabolite amounts targeted metabolomics is used to quantify the metabolites in the sample including the analyte classes of amino acids, biogenic amines, acylcarnitines, hexoses, sphingolipids and glycerophospholipids. The quantification is carried out using in the presence of isotopically labeled internal standards and determined by the methods as described above. A list of analytes including their abbreviations (BC codes) being suitable as metabolites to be measured according to the invention is indicated in the following Table 1.

TABLE 1

| BC code | Analyte |
|---|---|
| Table 1a: Amino acids and biogenic amines | |
| Ala | Alanine |
| Arg | Arginine |
| Asn | Asparagine |
| Asp | Aspartate |
| Cit | Citrulline |
| Gln | Glutamine |
| Glu | Glutamate |
| Gly | Glycine |
| His | Histidine |
| Ile | Isoleucine |
| Leu | Leucine |
| Lys | Lysine |
| Met | Methionine |
| Orn | Ornithine |
| Phe | Phenylalanine |
| Pro | Proline |
| Ser | Serine |
| Thr | Threonine |
| Trp | Tryptophane |
| Tyr | Tyrosine |
| Val | Valine |
| Ac-Orn | Acetylornithine |
| ADMA | Asymmetric dimethylarginine |
| SDMA | Symmetric dimethylarginine |
| total DMA | Total dimethylarginine |
| alpha-AAA | alpha-Aminoadipic acid |
| Carnosine | Carnosine |
| Creatinine | Creatinine |
| Histamine | Histamine |
| Kynurenine | Kynurenine |
| Met-SO | Methioninesulfoxide |

TABLE 1-continued

| BC code | Analyte |
|---|---|
| Nitro-Tyr | Nitrotyrosine |
| OH-Pro | Hydroxyproline |
| PEA | Phenylethylamine |
| Putrescine | Putrescine |
| Sarcosine | Sarcosine |
| Serotonin | Serotonin |
| Spermidine | Spermidine |
| Spermine | Spermine |
| Taurine | Taurine |

Table 1b: Acylcarnitines

| BC code | Analyte |
|---|---|
| C0 | Carnitine |
| C2 | Acetylcarnitine |
| C3 | Propionylcarnitine |
| C3:1 | Propenoylcarnitine |
| C3-OH | Hydroxypropionylcarnitine |
| C4 | Butyrylcarnitine |
| C4:1 | Butenylcarnitine |
| C4-OH (C3-DC) | Hydroxybutyrylcarnitine |
| C5 | Valerylcarnitine |
| C5:1 | Tiglylcarnitine |
| C5:1-DC | Glutaconylcarnitine |
| C5-DC (C6-OH) | Glutarylcarnitine* (Hydroxyhexanoylcarnitine) |
| C5-M-DC | Methylglutarylcarnitine |
| C5-OH (C3-DC-M) | Hydroxyvalerylcarnitine (Methylmalonylcarnitine) |
| C6 (C4:1-DC) | Hexanoylcarnitine (Fumarylcarnitine) |
| C6:1 | Hexenoylcarnitine |
| C7-DC | Pimelylcarnitine |
| C8 | Octanoylcarnitine |
| C9 | Nonaylcarnitine |
| C10 | Decanoylcarnitine |
| C10:1 | Decenoylcarnitine |
| C10:2 | Decadienylcarnitine |
| C12 | Dodecanoylcarnitine |
| C12:1 | Dodecenoylcarnitine |
| C12-DC | Dodecanedioylcarnitine |
| C14 | Tetradecanoylcarnitine |
| C14:1 | Tetradecenoylcarnitine |
| C14:1-OH | Hydroxytetradecenoylcarnitine |
| C14:2 | Tetradecadienylcarnitine |
| C14:2-OH | Hydroxytetradecadienylcarnitine |
| C16 | Hexadecanoylcarnitine |
| C16:1 | Hexadecenoylcarnitine |
| C16:1-OH | Hydroxyhexadecenoylcarnitine |
| C16:2 | Hexadecadienylcarnitine |
| C16:2-OH | Hydroxyhexadecadienylcarnitine |
| C16-OH | Hydroxyhexadecanoylcarnitine |
| C18 | Octadecanoylcarnitine |
| C18:1 | Octadecenoylcarnitine |
| C18:1-OH | Hydroxyoctadecenoylcarnitine |
| C18:2 | Octadecadienylcarnitine |
| C10:1 | Decenoylcarnitine |
| C10:2 | Decadienylcarnitine |
| C12 | Dodecanoylcarnitine |
| C12:1 | Dodecenoylcarnitine |
| C12-DC | Dodecanedioylcarnitine |
| C14 | Tetradecanoylcarnitine |
| C14:1 | Tetradecenoylcarnitine |
| C14:1-OH | Hydroxytetradecenoylcarnitine |
| C14:2 | Tetradecadienylcarnitine |
| C14:2-OH | Hydroxytetradecadienylcarnitine |
| C16 | Hexadecanoylcarnitine |

Table 1c: Hexoses

| BC code | Analyte |
|---|---|
| H1 | Hexose |

Table 1d: Sphingolipids

| BC code | Analyte |
|---|---|
| SM (OH) C14:1 | Hydroxysphingomyelin with acyl residue sum C14:1 |
| SM (OH) C16:1 | Hydroxysphingomyelin with acyl residue sum C16:1 |
| SM (OH) C22:1 | Hydroxysphingomyelin with acyl residue sum C22:1 |
| SM (OH) C22:2 | Hydroxysphingomyelin with acyl residue sum C22:2 |
| SM (OH) C24:1 | Hydroxysphingomyelin with acyl residue sum C24:1 |
| SM C16:0 | sphingomyelin with acyl residue sum C16:0 |
| SM C16:1 | sphingomyelin with acyl residue sum C16:1 |
| SM C18:0 | sphingomyelin with acyl residue sum C18:0 |
| SM C18:1 | sphingomyelin with acyl residue sum C18:1 |
| SM C20:2 | sphingomyelin with acyl residue sum C20:2 |
| SM C22:3 | sphingomyelin with acyl residue sum C22:3 |

TABLE 1-continued

| BC code | Analyte |
| --- | --- |
| SM C24:0 | sphingomyelin with acyl residue sum C24:0 |
| SM C24:1 | sphingomyelin with acyl residue sum C24:1 |
| SM C26:0 | sphingomyelin with acyl residue sum C26:0 |
| SM C26:1 | sphingomyelin with acyl residue sum C26:1 |

Table 1e: Glycerophospholipids

| BC code | Analyte |
| --- | --- |
| lysoPC a C14:0 | Lysophosphatidylcholine with acyl residue C14:0 |
| lysoPC a C16:0 | Lysophosphatidylcholine with acyl residue C16:0 |
| lysoPC a C16:1 | Lysophosphatidylcholine with acyl residue C16:1 |
| lysoPC a C17:0 | Lysophosphatidylcholine with acyl residue C17:0 |
| lysoPC a C18:0 | Lysophosphatidylcholine with acyl residue C18:0 |
| lysoPC a C18:1 | Lysophosphatidylcholine with acyl residue C18:1 |
| lysoPC a C18:2 | Lysophosphatidylcholine with acyl residue C18:2 |
| lysoPC a C20:3 | Lysophosphatidylcholine with acyl residue C20:3 |
| lysoPC a C20:4 | Lysophosphatidylcholine with acyl residue C20:4 |
| lysoPC a C24:0 | Lysophosphatidylcholine with acyl residue C24:0 |
| lysoPC a C26:0 | Lysophosphatidylcholine with acyl residue C26:0 |
| lysoPC a C26:1 | Lysophosphatidylcholine with acyl residue C26:1 |
| lysoPC a C28:0 | Lysophosphatidylcholine with acyl residue C28:0 |
| lysoPC a C28:1 | Lysophosphatidylcholine with acyl residue C28:1 |
| PC aa C24:0 | Phosphatidylcholine with diacyl residue sum C24:0 |
| PC aa C26:0 | Phosphatidylcholine with diacyl residue sum C26:0 |
| PC aa C28:1 | Phosphatidylcholine with diacyl residue sum C28:1 |
| PC aa C30:0 | Phosphatidylcholine with diacyl residue sum C30:0 |
| PC aa C30:2 | Phosphatidylcholine with diacyl residue sum C30:2 |
| PC aa C32:0 | Phosphatidylcholine with diacyl residue sum C32:0 |
| PC aa C32:1 | Phosphatidylcholine with diacyl residue sum C32:1 |
| PC aa C32:2 | Phosphatidylcholine with diacyl residue sum C32:2 |
| PC aa C32:3 | Phosphatidylcholine with diacyl residue sum C32:3 |
| PC aa C34:1 | Phosphatidylcholine with diacyl residue sum C34:1 |
| PC aa C34:2 | Phosphatidylcholine with diacyl residue sum C34:2 |
| PC aa C34:3 | Phosphatidylcholine with diacyl residue sum C34:3 |
| PC aa C34:4 | Phosphatidylcholine with diacyl residue sum C34:4 |
| PC aa C36:0 | Phosphatidylcholine with diacyl residue sum C36:0 |
| PC aa C36:1 | Phosphatidylcholine with diacyl residue sum C36:1 |
| PC aa C36:2 | Phosphatidylcholine with diacyl residue sum C36:2 |
| PC aa C36:3 | Phosphatidylcholine with diacyl residue sum C36:3 |
| PC aa C36:4 | Phosphatidylcholine with diacyl residue sum C36:4 |
| PC aa C36:5 | Phosphatidylcholine with diacyl residue sum C36:5 |
| PC aa C36:6 | Phosphatidylcholine with diacyl residue sum C36:6 |
| PC aa C38:0 | Phosphatidylcholine with diacyl residue sum C38:0 |
| PC aa C38:1 | Phosphatidylcholine with diacyl residue sum C38:1 |
| PC aa C38:3 | Phosphatidylcholine with diacyl residue sum C38:3 |
| PC aa C38:4 | Phosphatidylcholine with diacyl residue sum C38:4 |
| PC aa C38:5 | Phosphatidylcholine with diacyl residue sum C38:5 |
| PC aa C38:6 | Phosphatidylcholine with diacyl residue sum C38:6 |
| PC aa C40:1 | Phosphatidylcholine with diacyl residue sum C40:1 |
| PC aa C40:2 | Phosphatidylcholine with diacyl residue sum C40:2 |
| PC aa C40:3 | Phosphatidylcholine with diacyl residue sum C40:3 |
| PC aa C40:4 | Phosphatidylcholine with diacyl residue sum C40:4 |
| PC aa C40:5 | Phosphatidylcholine with diacyl residue sum C40:5 |
| PC aa C40:6 | Phosphatidylcholine with diacyl residue sum C40:6 |
| PC aa C42:0 | Phosphatidylcholine with diacyl residue sum C42:0 |
| PC aa C42:1 | Phosphatidylcholine with diacyl residue sum C42:1 |
| PC aa C42:2 | Phosphatidylcholine with diacyl residue sum C42:2 |
| PC aa C42:4 | Phosphatidylcholine with diacyl residue sum C42:4 |
| PC aa C42:5 | Phosphatidylcholine with diacyl residue sum C42:5 |
| PC aa C42:6 | Phosphatidylcholine with diacyl residue sum C42:6 |
| PC ae C30:0 | Phosphatidylcholine with acyl-alkyl residue sum C30:0 |
| PC ae C30:1 | Phosphatidylcholine with acyl-alkyl residue sum C30:1 |
| PC ae C30:2 | Phosphatidylcholine with acyl-alkyl residue sum C30:2 |
| PC ae C32:1 | Phosphatidylcholine with acyl-alkyl residue sum C32:1 |
| PC ae C32:2 | Phosphatidylcholine with acyl-alkyl residue sum C32:2 |
| PC ae C34:0 | Phosphatidylcholine with acyl-alkyl residue sum C34:0 |
| PC ae C34:1 | Phosphatidylcholine with acyl-alkyl residue sum C34:1 |
| PC ae C34:2 | Phosphatidylcholine with acyl-alkyl residue sum C34:2 |
| PC ae C34:3 | Phosphatidylcholine with acyl-alkyl residue sum C34:3 |
| PC ae C36:0 | Phosphatidylcholine with acyl-alkyl residue sum C36:0 |
| PC ae C36:1 | Phosphatidylcholine with acyl-alkyl residue sum C36:1 |
| PC ae C36:2 | Phosphatidylcholine with acyl-alkyl residue sum C36:2 |
| PC ae C36:3 | Phosphatidylcholine with acyl-alkyl residue sum C36:3 |
| PC ae C36:4 | Phosphatidylcholine with acyl-alkyl residue sum C36:4 |
| PC ae C36:5 | Phosphatidylcholine with acyl-alkyl residue sum C36:5 |
| PC ae C38:0 | Phosphatidylcholine with acyl-alkyl residue sum C38:0 |
| PC ae C38:1 | Phosphatidylcholine with acyl-alkyl residue sum C38:1 |
| PC ae C38:2 | Phosphatidylcholine with acyl-alkyl residue sum C38:2 |
| PC ae C38:3 | Phosphatidylcholine with acyl-alkyl residue sum C38:3 |
| PC ae C38:4 | Phosphatidylcholine with acyl-alkyl residue sum C38:4 |

TABLE 1-continued

| BC code | Analyte |
| --- | --- |
| PC ae C38:5 | Phosphatidylcholine with acyl-alkyl residue sum C38:5 |
| PC ae C38:6 | Phosphatidylcholine with acyl-alkyl residue sum C38:6 |
| PC ae C40:1 | Phosphatidylcholine with acyl-alkyl residue sum C40:1 |
| PC ae C40:2 | Phosphatidylcholine with acyl-alkyl residue sum C40:2 |
| PC ae C40:3 | Phosphatidylcholine with acyl-alkyl residue sum C40:3 |
| PC ae C40:4 | Phosphatidylcholine with acyl-alkyl residue sum C40:4 |
| PC ae C40:5 | Phosphatidylcholine with acyl-alkyl residue sum C40:5 |
| PC ae C40:6 | Phosphatidylcholine with acyl-alkyl residue sum C40:6 |
| PC ae C42:0 | Phosphatidylcholine with acyl-alkyl residue sum C42:0 |
| PC ae C42:1 | Phosphatidylcholine with acyl-alkyl residue sum C42:1 |
| PC ae C42:2 | Phosphatidylcholine with acyl-alkyl residue sum C42:2 |
| PC ae C42:3 | Phosphatidylcholine with acyl-alkyl residue sum C42:3 |
| PC ae C42:4 | Phosphatidylcholine with acyl-alkyl residue sum C42:4 |
| PC ae C42:5 | Phosphatidylcholine with acyl-alkyl residue sum C42:5 |
| PC ae C44:3 | Phosphatidylcholine with acyl-alkyl residue sum C44:3 |
| PC ae C44:4 | Phosphatidylcholine with acyl-alkyl residue sum C44:4 |
| PC ae C44:5 | Phosphatidylcholine with acyl-alkyl residue sum C44:5 |
| PC ae C44:6 | Phosphatidylcholine with acyl-alkyl residue sum C44:6 |

In the case of any lipids it should be noted that due to limitations of the mass resolution in the preferably employed MS/MS measurements the detected signal is a sum of several isobaric lipids with the same molecular weight (±0.5 Da range) within the same class. For example the signal of PC aa C36:6 can arise from different lipid species that have different fatty acid composition (e.g. PC 16:1/20:5 versus PC 18:4/18:2), various positioning of fatty acids sn-1/sn-2 (e.g. PC 18:4/18:2 versus PC 18:2/18:4) and different double bond positions and stereochemistry in those fatty acid chains (e.g. PC(18:4(6Z,9Z,12Z,15Z)/18:2(9Z,12Z)) versus PC(18:4(9E,11E,13E,15E)/18:2(9Z,12Z))).

Data Set

The data set for training the classifier consisted of 100 healthy patient control samples, 34 ovarian cancer samples and 80 early stage breast cancer samples, whereby one ovarian cancer sample was removed due to delayed plasma separation, as indicated by pre-analytical quality filtering, leading to 33 ovarian cancer samples. The ovarian cancer samples consisted of 2 FIGO Stage I, 1 FIGO Stage II, 28 FIGO stage III and 2 FIGO stage IV samples (Prat 2014). In the following FIGO stage I and II are designated as early stage ovarian cancer, whereas FIGO stage III and IV are designated as late stage ovarian cancer.

The data set for validating the classifier consisted of 50 healthy control samples, 35 ovarian cancer cases and 109 early stage breast cancer patients. In the validation set the ovarian cancer cases consisted of 5 FIGO stage I, 5 FIGO stage II, 15 FIGO stage III and 6 FIGO stage IV samples. Additionally, 4 samples do not feature any FIGO staging information.

Data Pre-Treatment

From the initial set of 188 metabolites measured by mass-spectrometry, 53 (28%) analytes were removed, since their concentration values were composed of more than 20% values below the limit of detection (LOD) either in the training dataset or in the validation dataset. The concentration of the remaining 135 metabolites was further filtered by three criteria i.e. (i) the fold change had to be higher than the coefficient of variance (CV) of replicated samples, (ii) the analytes needed to be significantly different in ovarian cancer patients versus healthy control samples in the training data set according to a t-test (p-value<0.05), or the random forest Mean Decrease Gini measure (as implemented in the R-package randomForest, available at http://cran.r-project.org/) had to be greater than 0.8, and (iii) no LOD value had to be present in the samples (Breiman 2001; Louppe, Gilles and Wehenkel, Louis and Sutera, Antonio and Geurts, Pierre 2013). These conservative filtering criteria led to 70 metabolites, which were enriched with 138 metabolite ratios, each consisting of a metabolite pair.

Feature Selection

For feature selection, only 31 serous ovarian cancer samples were used, therefore 2 endometrioid ovarian cancer samples were removed, in order to decrease biological heterogeneity. The resulting 208 features were then log 2 transformed and reduced by elastic net regularization regression analysis (Tibshirani et al. 2012) as implemented in the R-package "glmnet". Thereby, the model was trained on the training set for 100 alpha levels, ranging from 0 to 1, with a step size of 0.01. At each alpha level 10-fold cross validation was performed, in order to find the optimal fit. From the resulting optimal fits at 100 alpha levels the best one was chosen, by maximizing the sensitivity and specificity, plus minimizing the number of coefficients and the error obtained from the cross validation fits. This resulted in an optimal parametrized model fit with alpha level 96 and lambda level 0.285 consisting of a subset of 9 features consisting of in total 9 metabolites:

Ala, Arg, His, SM (OH) C24:1, Trp, lyso PC a C18:2, C18:2, Glu, PC aa C32:2

These features are composed of 5 single metabolites (Ala, Arg, His, SM (OH) C24:1, Trp) and 4 metabolite ratios (C18:2/lysoPC a C18:2, C18:2/SM (OH) C24:1, Glu/Ala, Glu/PC aa C32:2).

Classification

Ovarian Cancer Diagnosis

A random forest classifier was trained on this resulting set of 9 features, since it showed the best overall performance compared to other classifiers i.e. C5.0, generalized boosted regression modelling, logistic regression, or classification trees as implemented in the R-package caret (Max Kuhn; Jerome H. Friedman 2002; Jerome H. Friedman, Trevor Hastie, Rob Tibshirani 2009; Strobl et al. 2009; Steven L. Salzberg). Thus, the features were reduced to a smaller subset of features based on their variable importance measured with the Mean Decrease Gini importance measure. The obtained set of 3 features (C18.2/lysoPC a C18:2, Trp, Ala) consisting of 4 different metabolites was trained with random forest classification by repeated 10 fold cross validation, resulting in an area under the curve (AUC) of 1.0 (FIG. 1 left), a sensitivity of 100%, and a specificity of 100%.

Following training, the classifier was validated on an independent validation dataset described above. The classifier performance was evaluated by a receiver operator characteristic (ROC) curve, showing an AUC of 0.96 (FIG. 1 right) and by predicting the outcome with the fixed cut-off obtained in the training set leading to 88.5% sensitivity and 100% specificity. In detail, 31 of 35 ovarian cancer patients were correctly identified and 50 of 50 healthy controls were correctly identified. In a second step, we used this model to test the differential diagnosis and included breast cancer patient samples without metastasis for comparison. Thereby 104 of 109 of the breast cancer samples were identified as non-ovarian cancer, corresponding to a specificity of 96.8% and an AUC of 0.94 (FIG. 2). In order to evaluate the prediction power of the single features we investigated the prediction potential of each metabolite from the model as single metabolite and ratio in the training set (FIG. 3A) and in the validation set (FIG. 3B).

Early Stage Ovarian Cancer Diagnosis

The classifier performance on early stage ovarian cancer patients (10 patients in total) was evaluated by a receiver operator characteristic (ROC) curve, showing an AUC of 0.98 (FIG. 4 left) and by predicting the outcome with the fixed cut-off obtained in the training set leading to 90% sensitivity and 100% specificity. In detail, 9 of 10 early stage ovarian cancer patients were correctly identified. Differential diagnosis including breast cancer patients without metastasis for comparison shows an AUC of 0.97 (FIG. 4 right). In order to evaluate the prediction power of the single features we investigated the prediction potential of each metabolite from the model as single metabolite and ratio in the training set (FIG. 5A) and in the validation set (FIG. 5B).

Late Stage Ovarian Cancer Diagnosis

The classifier performance on late stage ovarian cancer patients (25 patients in total) was evaluated by a receiver operator characteristic (ROC) curve, showing an AUC of 0.95 (FIG. 6 left) and by predicting the outcome with the fixed cut-off obtained in the training set leading to 88% sensitivity and 100% specificity. In detail, 22 of 25 late stage ovarian cancer patients were correctly. Differential diagnosis including breast cancer patients without metastasis for comparison shows an AUC of 0.92 (FIG. 6 right). In order to evaluate the prediction power of the single features we investigated the prediction potential of each metabolite from the model as a single metabolite and ratio in the training set (FIG. 7A) and in the validation set (FIG. 7B).

BRIEF DESCRIPTION OF THE FIGURES

In the annex of the specification reference is made to the following FIGS. 1-7.

Performance on the training set is shown to the left whereas the performance on the validation set is shown to the right. The continuous line with the dot represents the discrimination power of the classifier, whereby the filled circle (threshold) is calculated by $(1-\text{sensitivity})^2+(1-\text{specificity})^2$. The x-axis and y-axis show the false positive rate and the true positive rate, respectively. The dash-dotted diagonal line indicates no discrimination power, i.e. random classification.

Figure 1:
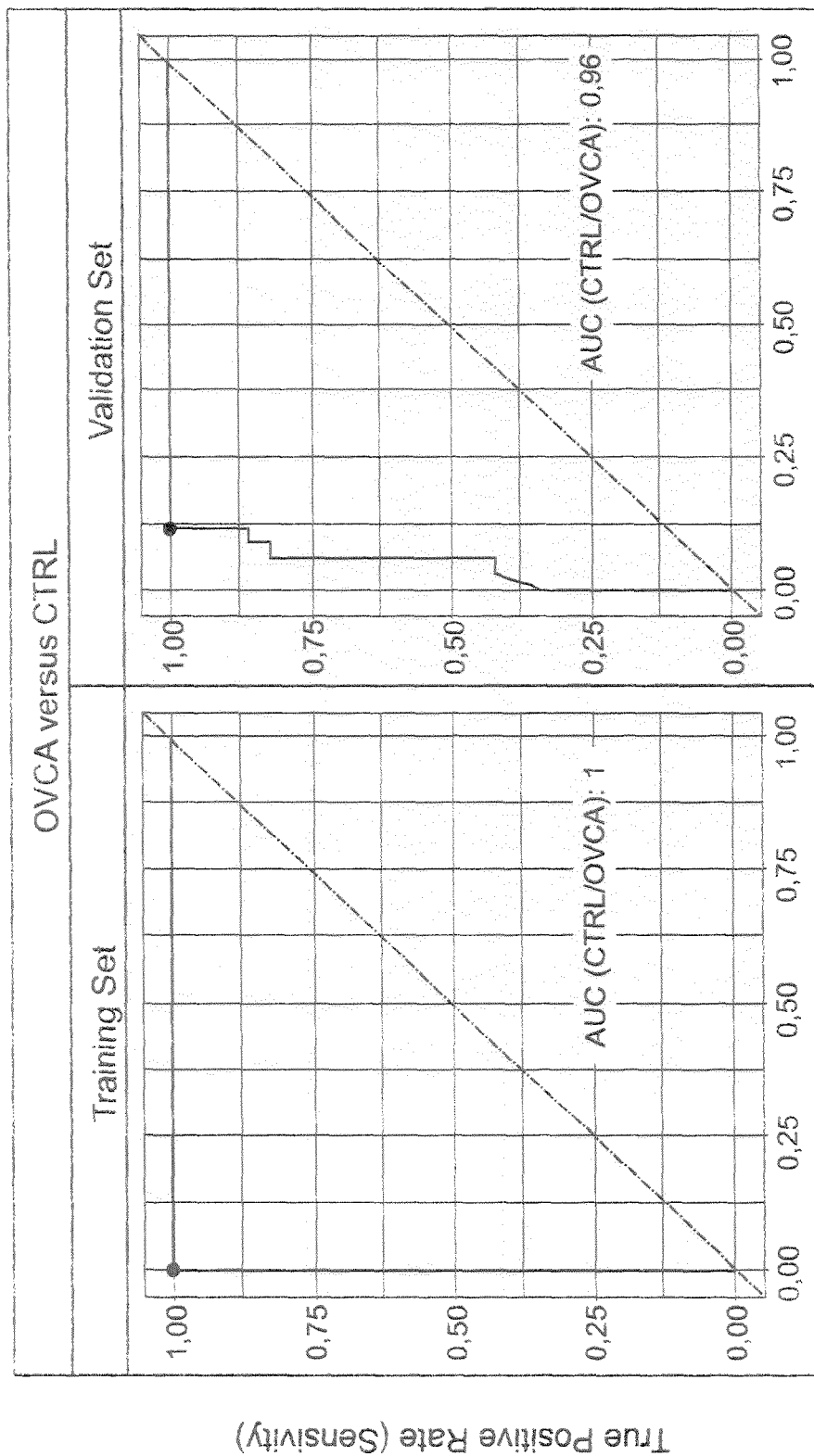
FIG. 1: Receiver operating characteristics (ROC) curve of the classifier for the differentiation between healthy controls (CTRL) and ovarian cancer patients (OVCA).
Figure 2:
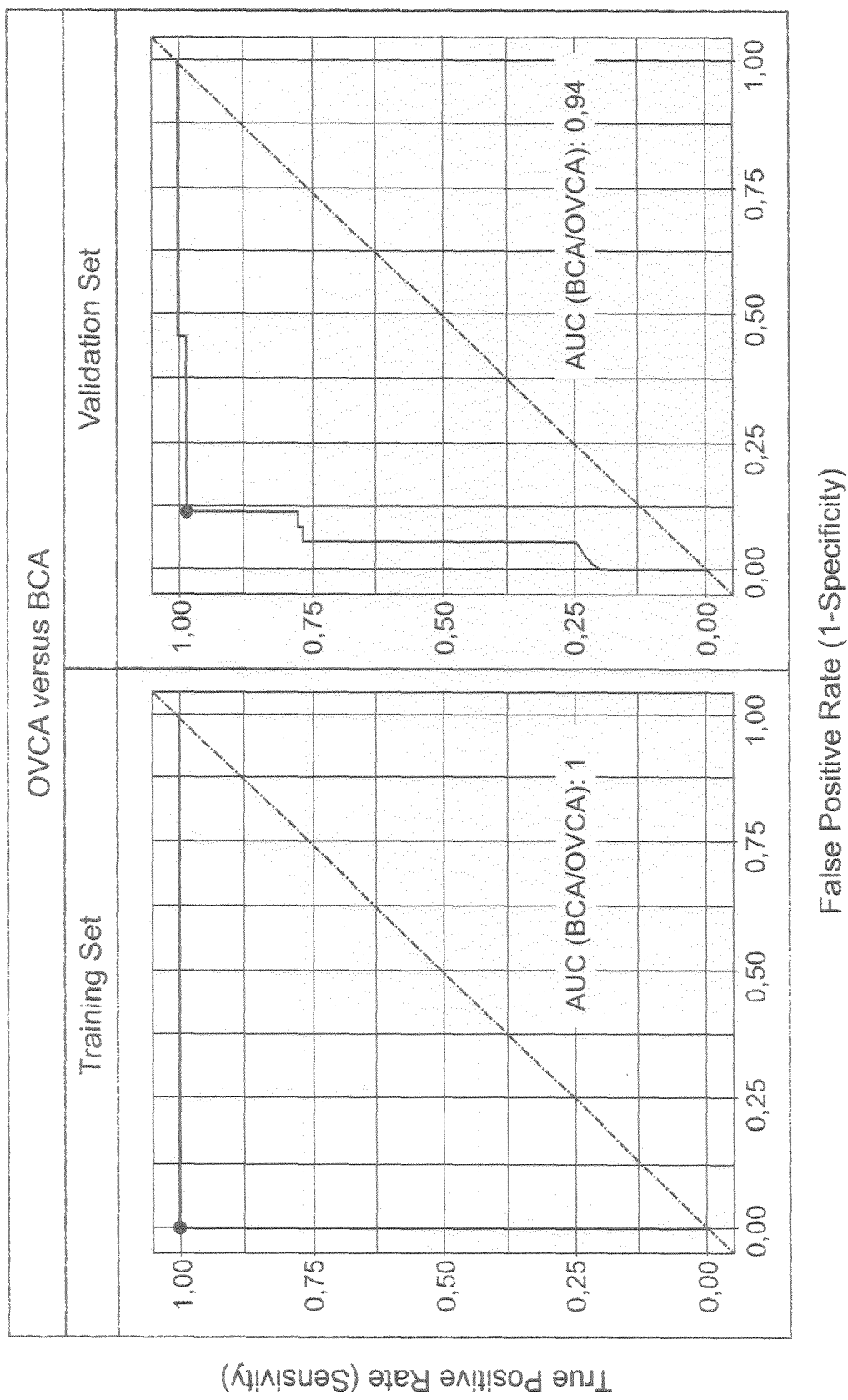

FIG. 2: Receiver operating characteristics (ROC) curve of the classifier for the differential diagnosis between ovarian cancer patients (OVCA) and breast cancer patients (BCA). Performance on the training set is shown to the left, whereas the performance on the validation set is shown to the right. The continuous line with the dot represents the discrimination power of the classifier, whereby the filled circle (threshold) is calculated by $(1-\text{sensitivity})^2+(1-\text{specificity})^2$. The x-axis and y-axis show the false positive rate and the true positive rate, respectively. The dash-dotted diagonal line indicates no discrimination power, i.e. random classification.

Figure 3A:
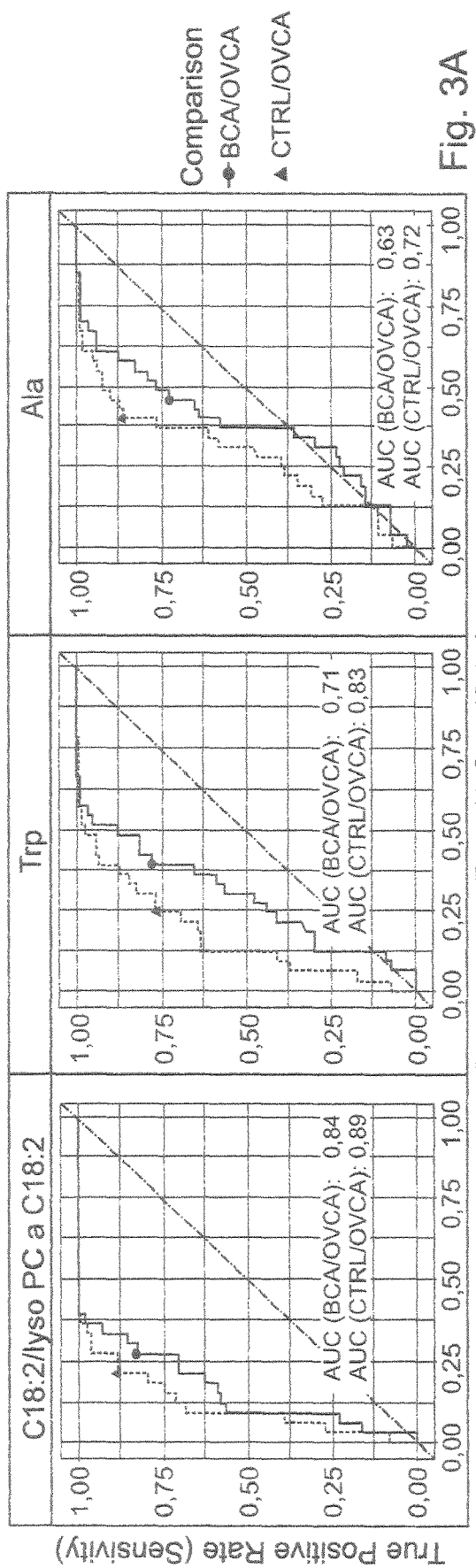
Figure 3B:
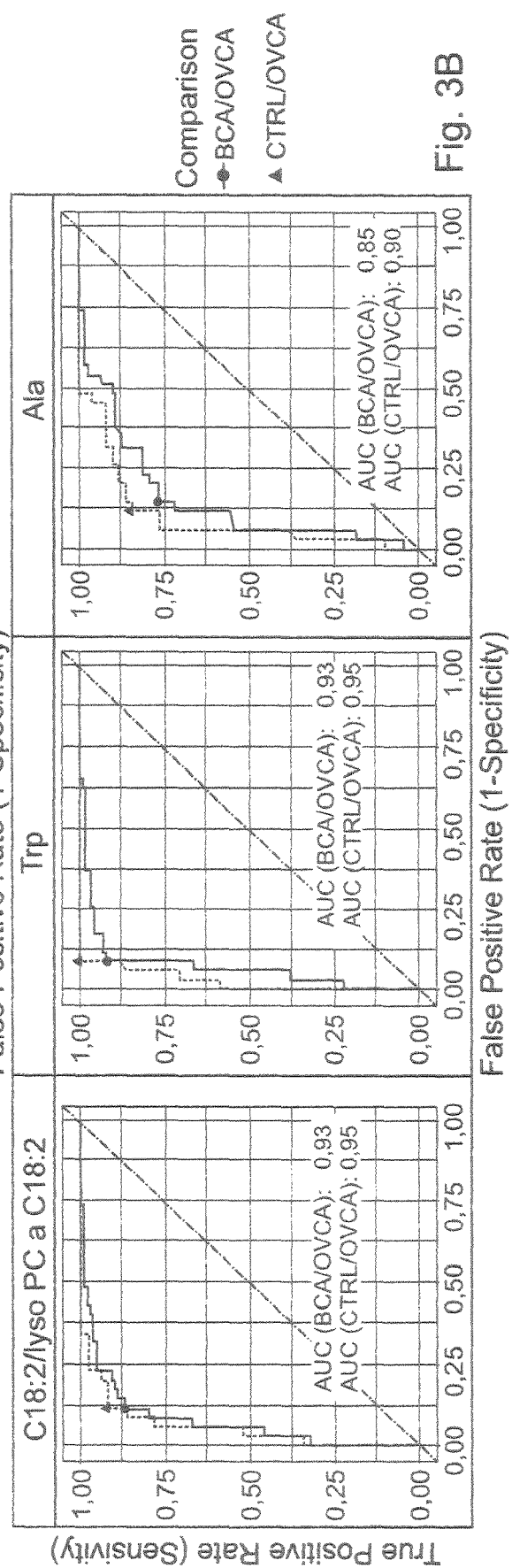

FIG. 3: Receiver operating characteristics (ROC) curve in (A) training data and (B) validation data of the single features from left to right (C18:2/lyso PC a C18:2, Trp, Ala).

ROC curve of the differential diagnosis between ovarian cancer patients (OVCA) and breast cancer patients (BCA) is shown as a continuous line with a cut-off point, depicted as filled circle. ROC curve of the differentiation between healthy controls (CTRL) and ovarian cancer patients (OVCA) is shown as dashed line with a filled triangle as cut-off indication. All cut-off points are calculated by $(1-\text{sensitivity})^2+(1-\text{specificity})^2$. The x-axis and y-axis show the false positive rate and the true positive rate, respectively. The dash-dotted diagonal line indicates no discrimination power, i.e. random classification.

Figure 4:
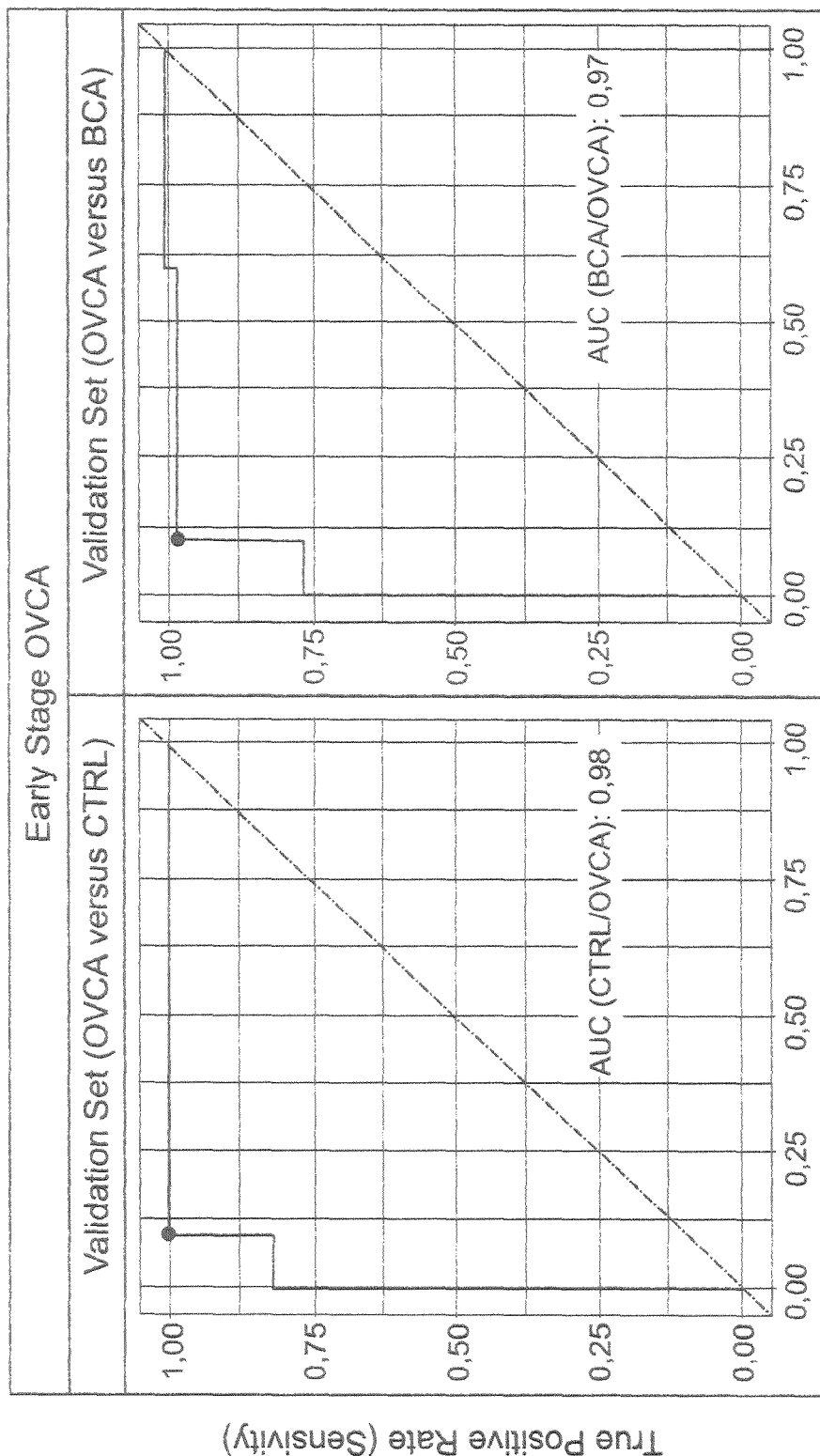

FIG. 4: Left: Receiver operating characteristics (ROC) curve of the classifier performance on the validation set for the differentiation between healthy controls (CTRL) and early stage ovarian cancer patients (OVCA). Right: ROC curve of the classifier performance on the validation set for differentiation between early stage breast cancer patients (BCA) and early stage ovarian cancer patients (OVCA).

The continuous line with the filled circle (threshold) represents the discrimination power of the classifier, whereby the filled circle is calculated by $(1-\text{sensitivity})^2+(1-\text{specificity})^2$. The x-axis and y-axis show the false positive rate and the true positive rate, respectively. The dash-dotted diagonal line indicates no discrimination power, i.e. random classification.

Figure 5A:
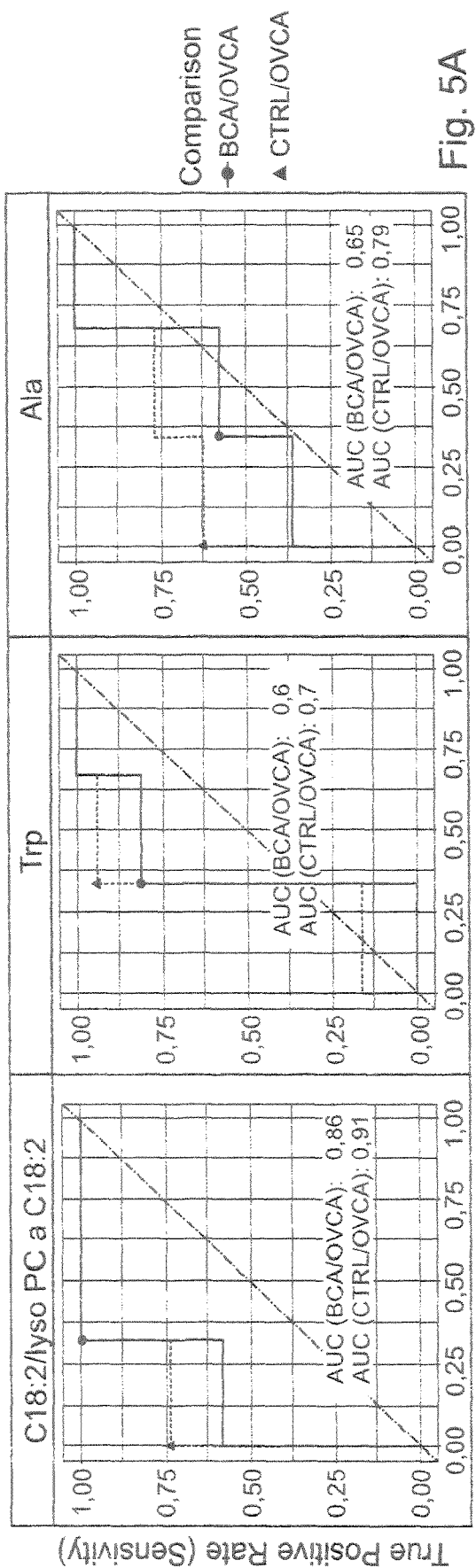
Figure 5B:
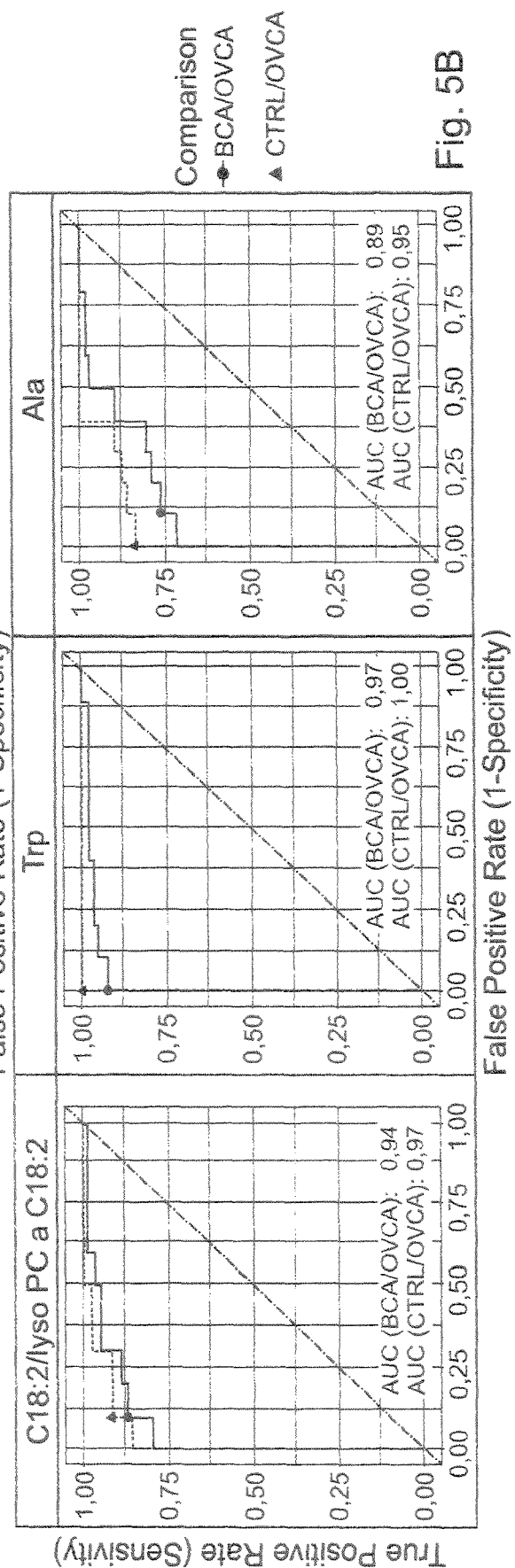

FIG. 5: Receiver operating characteristics (ROC) curves in (A) training data and (B) validation data of the single features in early stage ovarian cancer from left to right (C18:2/lyso PC a C18:2, Trp, Ala) of the classifier. ROC curve of the differential diagnostic between early stage ovarian cancer patients (OVCA) and early stage breast cancer patients (BCA) is shown as continuous line with a cut-off point, depicted as filled circle. ROC curve of the differentiation between healthy controls (CTRL) and early stage ovarian cancer patients (OVCA) is shown as dashed line with a filled triangle as cut-off indication. All cut-off points are calculated by $(1-\text{sensitivity})^2+(1-\text{specificity})^2$. The x-axis and y-axis show the false positive rate and the true positive rate, respectively. The dash-dotted diagonal line indicates no discrimination power, i.e. random classification.

Figure 6:
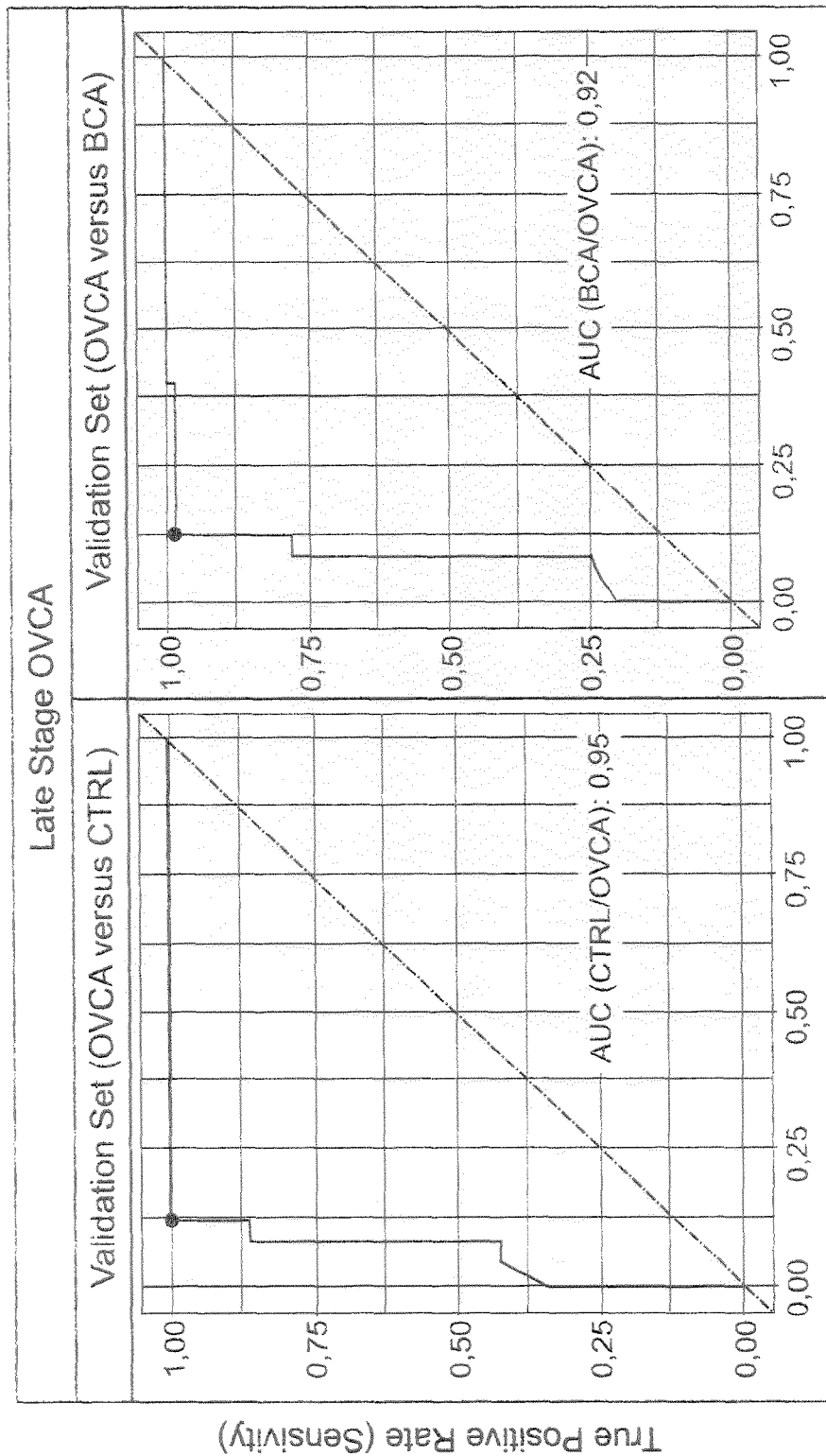

FIG. 6: Left: Receiver operating characteristics (ROC) curve of the classifier performance on the validation set for the differentiation between healthy controls (CTRL) and late stage ovarian cancer patients (OVCA). Right: Receiver operating characteristics (ROC) curve of the classifier performance on the validation set for the differentiation between early stage breast cancer patients (BCA) and late stage ovarian cancer patients (OVCA). The continuous line with the filled circle (threshold) represents the discrimination power of the classifier, whereby the filled circle is calculated by $(1-\text{sensitivity})^2+(1-\text{specificity})^2$. The x-axis and y-axis show the false positive rate and the true positive rate, respectively. The dash-dotted diagonal line indicates no discrimination power, i.e. random classification.

FIG. 7: Receiver operating characteristics (ROC) curve in (A) training data and (B) validation data of the single features in early stage ovarian cancer from left to right (C18:2/lyso PC a C18:2, Trp, Ala) of the classifier. ROC curve of the differential diagnostic between late stage ovarian cancer patients (OVCA) and early stage breast cancer patients (BCA) is shown as continuous line with a cut-off point, depicted as filled circle. ROC curve of the differentiation between healthy controls (CTRL) and late stage ovarian cancer patients (OVCA) is shown as dashed line with a filled triangle as cut-off indication. All cut-off points are calculated by $(1-\text{sensitivity})^2+(1-\text{specificity})^2$. The x-axis and y-axis show the false positive rate and the true positive rate, respectively. The dash-dotted diagonal line indicates no discrimination power, i.e. random classification.

FIG. 8: Receiver operating characteristics (ROC) curve in (A) training data and (B) validation data of the single features from left to right (Glu/PC aa C32:2, C18:2/SM (OH) C24:1, Glu/Ala).

ROC curve of the differential diagnosis between ovarian cancer patients (OVCA) and breast cancer patients (BCA) is shown as a continuous line with a cut-off point, depicted as filled circle. ROC curve of the differentiation between healthy controls (CTRL) and ovarian cancer patients (OVCA) is shown as dashed line with a filled triangle as cut-off indication. All cut-off points are calculated by $(1-\text{sensitivity})2+(1-\text{specificity})2$. The x-axis and y-axis show the false positive rate and the true positive rate, respectively. The dash-dotted diagonal line indicates no discrimination power, i.e. random classification.

Figure 9:
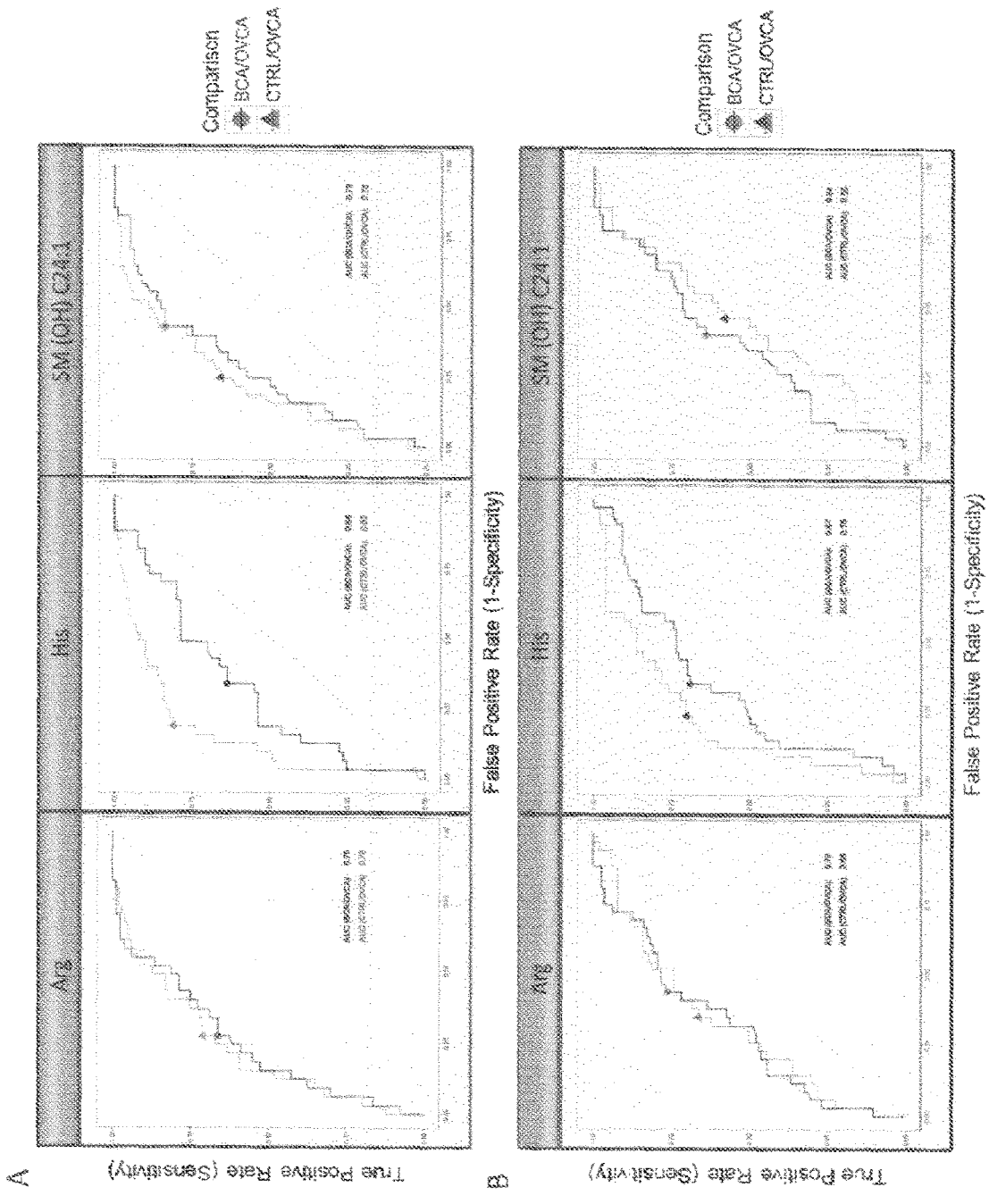

FIG. 9: Receiver operating characteristics (ROC) curve in (A) training data and (B) validation data of the single features from left to right (Arg, His, SM (OH) C24:1).

ROC curve of the differential diagnosis between ovarian cancer patients (OVCA) and breast cancer patients (BCA) is shown as a continuous line with a cut-off point, depicted as filled circle. ROC curve of the differentiation between healthy controls (CTRL) and ovarian cancer patients (OVCA) is shown as dashed line with a filled triangle as cut-off indication. All cut-off points are calculated by $(1-\text{sensitivity})2+(1-\text{specificity})2$. The x-axis and y-axis show the false positive rate and the true positive rate, respectively. The dash-dotted diagonal line indicates no discrimination power, i.e. random classification.

REFERENCES

Bairey, Osnat; Blickstein, Dorit; Stark, Pinhas; Prokocimer, Miron; Nativ, Hila Magen; Kirgner, Ilia; Shaklai, Mati (2003): Serum CA 125 as a prognostic factor in non-Hodgkin's lymphoma. In: *Leukemia & lymphoma* 44 (10), S. 1733-1738. DOI: 10.1080/1042819031000104079.

Berkenblit, Anna; Cannistra, Stephen A. (2005): Advances in the management of epithelial ovarian cancer. In: *The Journal of reproductive medicine* 50 (6), S. 426-438.

Breiman, L. (2001): Random Forests, Machine Learning.

Jerome H. Friedman (2002): Stochastic gradient boosting. In: *Journal Computational Statistics & Data Analysis*, S. 367-378. DOI: 10.1016/S0167-9473(01)00065-2.

Jerome H. Friedman, Trevor Hastie, Rob Tibshirani (2009): Regularization Paths for Generalized Linear Models via Coordinate Descent. In: *Journal of Statistical Software*. DOI: 10.18637/jss.v033.i01.

Kitawaki, Jo; Ishihara, Hiroaki; Koshiba, Hisato; Kiyomizu, Miyo; Teramoto, Mariko; Kitaoka, Yui; Honjo, Hideo (2005): Usefulness and limits of CA-125 in diagnosis of endometriosis without associated ovarian endometriomas. In: *Human reproduction (Oxford, England)* 20 (7), S. 1999-2003. DOI: 10.1093/humrep/deh890.

Louppe, Gilles and Wehenkel, Louis and Sutera, Antonio and Geurts, Pierre (2013): Understanding Variable Importances in Forests of Randomized Trees. Proceedings of the 26th International Conference on Neural Information Processing Systems.

Max Kuhn: Building Predictive Models in R Using the caret Package. In: *Journal of Statistical Software* 2008. DOI: 10.18637/jss.v028.i05.

Moore, Richard G.; Miller, M. Craig; Disilvestro, Paul; Landrum, Lisa M.; Gajewski, Walter; Ball, John J.; Skates, Steven J. (2011): Evaluation of the diagnostic accuracy of the risk of ovarian malignancy algorithm in women with a pelvic mass. In: *Obstetrics and gynecology* 118 (2 Pt 1), S. 280-288. DOI: 10.1097/AOG.0b013e318224fce2.

Norum, L. F.; Erikstein, B.; Nustad, K. (2001): Elevated CA125 in breast cancer—A sign of advanced disease. In: *Tumour biology: the journal of the International Society for Oncodevelopmental Biology and Medicine* 22 (4), S. 223-228.

Prat, Jaime (2014): Staging classification for cancer of the ovary, fallopian tube, and peritoneum. In: *International journal of gynaecology and obstetrics: the official organ of the International Federation of Gynaecology and Obstetrics* 124 (1), S. 1-5. DOI: 10.1016/j.ijgo.2013.10.001.

Roupa, Zoi; Faros, Efthimios; Raftopoulos, Vasilios; Tzavelas, Georgios; Kotrotsiou, Evangelia; Sotiropoulou, Penelope et al. (2004): Serum CA 125 combined with transvaginal ultrasonography for ovarian cancer screening. In: *In vivo (Athens, Greece)* 18 (6), S. 831-836.

Shapira, I.; Oswald, M.; Lovecchio, J.; Khalili, H.; Menzin, A.; Whyte, J. et al. (2014): Circulating biomarkers for detection of ovarian cancer and predicting cancer outcomes. In: *British journal of cancer* 110 (4), S. 976-983. DOI: 10.1038/bjc.2013.795.

Siegel, Rebecca L.; Miller, Kimberly D.; Jemal, Ahmedin (2015): Cancer statistics, 2015. In: *CA: a cancer journal for clinicians* 65 (1), S. 5-29. DOI: 10.3322/caac.21254.

Steven L. Salzberg: C4.5: Programs for Machine Learning. In: *Machine Learning* 1994. DOI: 10.1007/BF00993309.

Strobl, Carolin; Malley, James; Tutz, Gerhard (2009): An introduction to recursive partitioning: rationale, application, and characteristics of classification and regression trees, bagging, and random forests. In: *Psychological methods* 14 (4), S. 323-348. DOI: 10.1037/a0016973.

Suh, K. Stephen; Park, Sang W.; Castro, Angelica; Patel, Hiren; Blake, Patrick; Liang, Michael; Goy, Andre (2010): Ovarian cancer biomarkers for molecular biosensors and translational medicine. In: *Expert review of molecular diagnostics* 10 (8), S. 1069-1083. DOI: 10.1586/erm.10.87.

Tibshirani, Robert; Bien, Jacob; Friedman, Jerome; Hastie, Trevor; Simon, Noah; Taylor, Jonathan; Tibshirani, Ryan J. (2012): Strong rules for discarding predictors in lasso-type problems. In: *Journal of the Royal Statistical Society. Series B, Statistical methodology* 74 (2), S. 245-266. DOI: 10.1111/j.1467-9868.2011.01004.x.

Vaughan, Sebastian; Coward, Jermaine I.; Bast, Robert C.; Berchuck, Andy; Berek, Jonathan S.; Brenton, James D. et al. (2011): Rethinking ovarian cancer: recommendations for improving outcomes. In: *Nature reviews. Cancer* 11 (10), S. 719-725. DOI: 10.1038/nrc3144.

Wei, S. U.; Li, Hui; Zhang, Bei (2016): The diagnostic value of serum HE4 and CA-125 and ROMA index in ovarian cancer. In: *Biomedical reports* 5 (1), S. 41-44. DOI: 10.3892/br.2016.682.

Yamamoto, Manabu; Baba, Hideo; Toh, Yasushi; Okamura, Takeshi; Maehara, Yoshihiko (2007): Peritoneal lavage CEA/CA125 is a prognostic factor for gastric cancer patients. In: *Journal of cancer research and clinical oncology* 133 (7), S. 471-476. DOI: 10.1007/500432-006-0189-2.

The invention claimed is:

1. A method for assessing ovarian cancer in a patient comprising quantifying in a sample from the patient an amount of
   i.) at least one amino acid selected from the group of alanine, arginine, histidine, tryptophan, and glutamate,
   ii.) one phospholipid selected from the group of lyso PC a C18:1, lyso PC a C18:2, and PC aa C32:2,
   iii.) one acylcarnitine selected from the group of acylcarnitine C18:1 and acylcarnitine C18:2,
   iv.) optionally one sphingolipid SM(OH)C24:1, and
   v.) determining at least one ratio of at least two biomarkers of i), ii), iii), and iv), the at least one ratio selected from C18:2/lysoPC a C18:2, C18:2/SM (OH) C24:1, Glu/Ala, and Glu/PC aa C32:2,
   wherein each amount and ratio has a threshold with at least 88% sensitivity and 100% specificity for ovarian cancer,
diagnosing the patient with ovarian cancer when the amount of each biomarker and the at least one ratio is equal to or exceeds its threshold, and administering to the patient diagnosed with ovarian cancer a treatment comprising at least one of chemotherapy, debulking surgery and a pharmaceutical therapeutic agent capable of treating ovarian cancer.

2. The method according to claim 1, wherein arginine and tryptophan are quantified and the ratio of C18:2/lysoPC a C18:2 is determined.

3. The method according to claim 1, wherein the patient is a symptomatic and/or asymptomatic patient.

4. The method according to claim 1, wherein the quantifying is based on a quantitative analytical method selected from chromatography, spectroscopy, and/or mass spectrometry.

5. The method according to claim 4, wherein chromatography comprises at least one of GC, LC, HPLC, or UPLC; spectroscopy comprises at least one of UV/Vis, IR, or NMR; and mass spectrometry comprises at least one of ESI-QqQ, ESI-QqTOF, MALDI-QqQ, MALDI-QqTOF, or MALDI-TOF-TOF.

6. The method according to claim 1, wherein the sample is blood, serum, and/or plasma.

7. The method according to claim 1, wherein the patient is diagnosed with early stage ovarian cancer.

8. The method according to claim 1, wherein the patient is diagnosed with late stage ovarian cancer.

9. The method according to claim 1, wherein the patient is previously diagnosed with ovarian cancer, the method further comprising diagnosing the patient with progressing ovarian cancer.

* * * * *